(12) United States Patent
Haider et al.

(10) Patent No.: US 11,168,041 B2
(45) Date of Patent: Nov. 9, 2021

(54) EFFICIENT DOWNSTREAM PROCESS FOR N-BUTANE DEHYDROGENATION TECHNOLOGY FOR THE PRODUCTION OF HIGH PURITY BUTYLENES

(71) Applicant: SABIC Global Technologies B.V., Bergen op Zoom (NL)

(72) Inventors: Muhammad H. Haider, Riyadh (SA); Abdulaziz Al-Zahrani, Riyadh (SA); Ahmed S. Al-Zenaidi, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/263,265

(22) PCT Filed: Jun. 19, 2019

(86) PCT No.: PCT/IB2019/055173
§ 371 (c)(1),
(2) Date: Jan. 26, 2021

(87) PCT Pub. No.: WO2020/030995
PCT Pub. Date: Feb. 13, 2020

(65) Prior Publication Data
US 2021/0139395 A1 May 13, 2021

Related U.S. Application Data

(60) Provisional application No. 62/715,182, filed on Aug. 6, 2018.

(51) Int. Cl.
*C07C 7/08* (2006.01)
*B01D 3/40* (2006.01)
(Continued)

(52) U.S. Cl.
CPC ............ *C07C 7/08* (2013.01); *B01D 3/40* (2013.01); *C07C 5/333* (2013.01); *C07C 7/005* (2013.01); *C07C 7/10* (2013.01)

(58) Field of Classification Search
CPC .. C07C 7/08; C07C 7/10; C07C 5/333; C07C 7/005; B01D 3/40
See application file for complete search history.

(56) References Cited

U.S. PATENT DOCUMENTS 2,552,198 A * 5/1951 Mayland .................. C07C 7/10
585/838
4,558,168 A 12/1985 Gussow et al.
(Continued)

FOREIGN PATENT DOCUMENTS

EP 1322581 A1 7/2003
EP 2809633 B1 12/2015
(Continued)

OTHER PUBLICATIONS

International Search Report and Written Opinion from PCT/IB2019/055173 dated Nov. 13, 2019, 9 pages.
(Continued)

*Primary Examiner* — Thuan D Dang
(74) *Attorney, Agent, or Firm* — Norton Rose Fulbright US LLP

(57) ABSTRACT

A method for producing butenes by the dehydrogenation of n-butane includes dehydrogenating the n-butane in a dehydrogenation zone and contacting material from the dehydrogenation zone with a solvent that is more selective to dissolve n-butane than butenes. The resulting fluid from the contacting is subjected to extractive distillation to produce (1) a stream comprising a solution of the n-butane and solvent and (2) a stream comprising the butenes.

19 Claims, 2 Drawing Sheets

(51) Int. Cl.
*C07C 5/333* (2006.01)
*C07C 7/00* (2006.01)
*C07C 7/10* (2006.01)

(56) References Cited

U.S. PATENT DOCUMENTS

| | | |
|---|---|---|
| 7,485,761 B2 | 2/2009 | Schindler et al. |
| 7,518,024 B2 | 4/2009 | Schindler et al. |
| 8,420,879 B2 | 4/2013 | Kostova et al. |
| 9,193,647 B2 | 11/2015 | Giesa et al. |

FOREIGN PATENT DOCUMENTS

| | | |
|---|---|---|
| GB | 881597 A | 11/1961 |
| RU | 2165913 C2 | 4/2001 |
| WO | WO0224614 A1 | 3/2002 |
| WO | WO2005042449 A1 | 5/2005 |

OTHER PUBLICATIONS

Ndiaye et al. "Phase behavior of olive and soybean oils in compressed propane and n-butane." Brazilian J. Chem. Eng. 23 (03) (2006) 405-415.
Novello et al. "Kinetics of pure propane and n-butane desorption from soybean oil." Canadian J. Chem. Eng. 91 (2013) 1945-1949.
Tres et al. "Low-pressure solubility of propane and n-butane in refined soybean oil." J. Chem. Thermodynamics 41 (2009) 1378-1381.
Tres et al. "Separation of n-butane from soybean oil mixtures using membrane processes." J. Membrane Science 333 (2009) 141-146.
Tres et al. "Solvent recovery from soybean oil/n-butane mixtures using a hollow fiber ultrafiltration membrane," Brazilian J. Chem. Eng. 31 (01) (2014) 243-249.

* cited by examiner

EFFICIENT DOWNSTREAM PROCESS FOR N-BUTANE DEHYDROGENATION TECHNOLOGY FOR THE PRODUCTION OF HIGH PURITY BUTYLENES

CROSS REFERENCE TO RELATED APPLICATIONS

This application is a national phase application under 35 U.S.C. § 371 of International Application No. PCT/IB2019/055173 filed Jun. 19, 2019, which claims priority to U.S. Provisional Patent Application No. 62/715,182 filed Aug. 6, 2018. The entire contents of each of the above-referenced disclosures is specifically incorporated by reference herein without disclaimer.

FIELD OF INVENTION

The present invention generally relates to the production of butylenes (butenes). More specifically, the present invention involves dehydrogenating n-butane and then separating the mixture of materials resulting from that dehydrogenation by a method that includes using a solvent to form a solution with unreacted n-butane and separating that solution from butenes formed by the dehydrogenation.

BACKGROUND OF THE INVENTION

Implementation of n-butane dehydrogenation technology for the production of butenes (1-butene and 2-butene) on an industrial scale has not been widely achieved because of un-economical processes downstream the dehydrogenation reactor. It is fairly common that product formed by the n-butane dehydrogenation reaction mainly consists of 2-butene (cis and trans) and 1-butene, along with very minor amounts of butadiene and isobutylene. Very close boiling points (BPs) of components, namely the unreacted feed (n-butane, BP of −1° C.) and products (trans 2-butene, BP of 0.9° C.), makes separation of the product from the unreacted feed by normal distillation columns economically unfeasible. This has a major impact on the capital expenditure of the industrial scale manufacturing of butenes from normal butane dehydrogenation. In order to make this technology robust enough to be realized on the industrial scale, an efficient process downstream the dehydrogenation reactor is needed.

BRIEF SUMMARY OF THE INVENTION

A method has been discovered that provides a solution to at least some of the problems associated with producing butenes from the dehydrogenation of n-butane. The solution is an efficient, robust, and economically feasible process downstream the reactor through which unconverted normal butane (feed), of the dehydrogenation process, can be successfully separated from n-butane product. The method involves the use of a solvent for dissolving un-converted n-butane and separating the resulting solution from the butene product. Solvents that are more selective to dissolve n-butane than butenes, such as soya bean oil, can be used to carry out the invention.

Embodiments of the invention include a method of producing butane. The method includes dehydrogenating, in a dehydrogenation reactor, a feed stream comprising primarily n-butane to produce an intermediate product stream comprising n-butane and one or more butenes. The method also includes contacting the intermediate product stream with a solvent that is more selective for dissolving the n-butane than for dissolving the one or more butenes to form a fluid that comprises (1) a first portion comprising primarily the solvent and the n-butane, collectively, and (2) a second portion comprising primarily the one or more butenes. The method further includes separating the fluid to produce a recycle stream comprising primarily the solvent and the n-butane, collectively, and a product stream comprising primarily the one or more butenes.

Embodiments of the invention include a method of producing butane. The method includes dehydrogenating, in a dehydrogenation reactor, a feed stream comprising primarily n-butane to produce an intermediate product stream comprising n-butane and one or more butenes. The method also includes flowing the intermediate product stream to an extractive distillation column in which soya bean oil is disposed. The method further includes contacting the intermediate product stream with the soya bean oil, the soya bean oil being more selective for dissolving the n-butane than for dissolving the one or more butenes, the contacting forming a fluid that comprises (1) a first portion comprising primarily the soya bean oil and the n-butane, collectively, and (2) a second portion comprising primarily the one or more butenes. The method includes distilling the fluid in the extractive distillation column under conditions sufficient to produce an extractor overhead stream comprising primarily the soya bean oil and the n-butane, collectively, and an extractor bottom stream comprising primarily the one or more butenes and separating the extractor overhead stream into a n-butane recycle stream comprising primarily n-butane and a recovered soybean oil stream comprising primarily soybean oil. The method further includes feeding the n-butane recycle stream to the dehydrogenation reactor and processing the extractor bottom stream to form a product comprising 92 wt. % to 99.7 wt. % butene.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %," "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

A method has been discovered for producing butenes by the dehydrogenation of n-butane. In the method, a solvent is used to dissolve un-converted n-butane and the resulting solution is then separated from butene formed by the dehydrogenation process. Solvents that more easily dissolve n-butane than butenes, such as soya bean oil, can be used to carry out the invention. In this way, according to embodiments of the invention, from an n-butane dehydrogenation reaction, the method can produce 1-butene and 2-butene at purity levels of 99.7 wt. % and 92 wt. %, respectively. The method addresses the major challenge of separating n-butane from butene products caused by the close boiling points of these materials.

Figure 1:
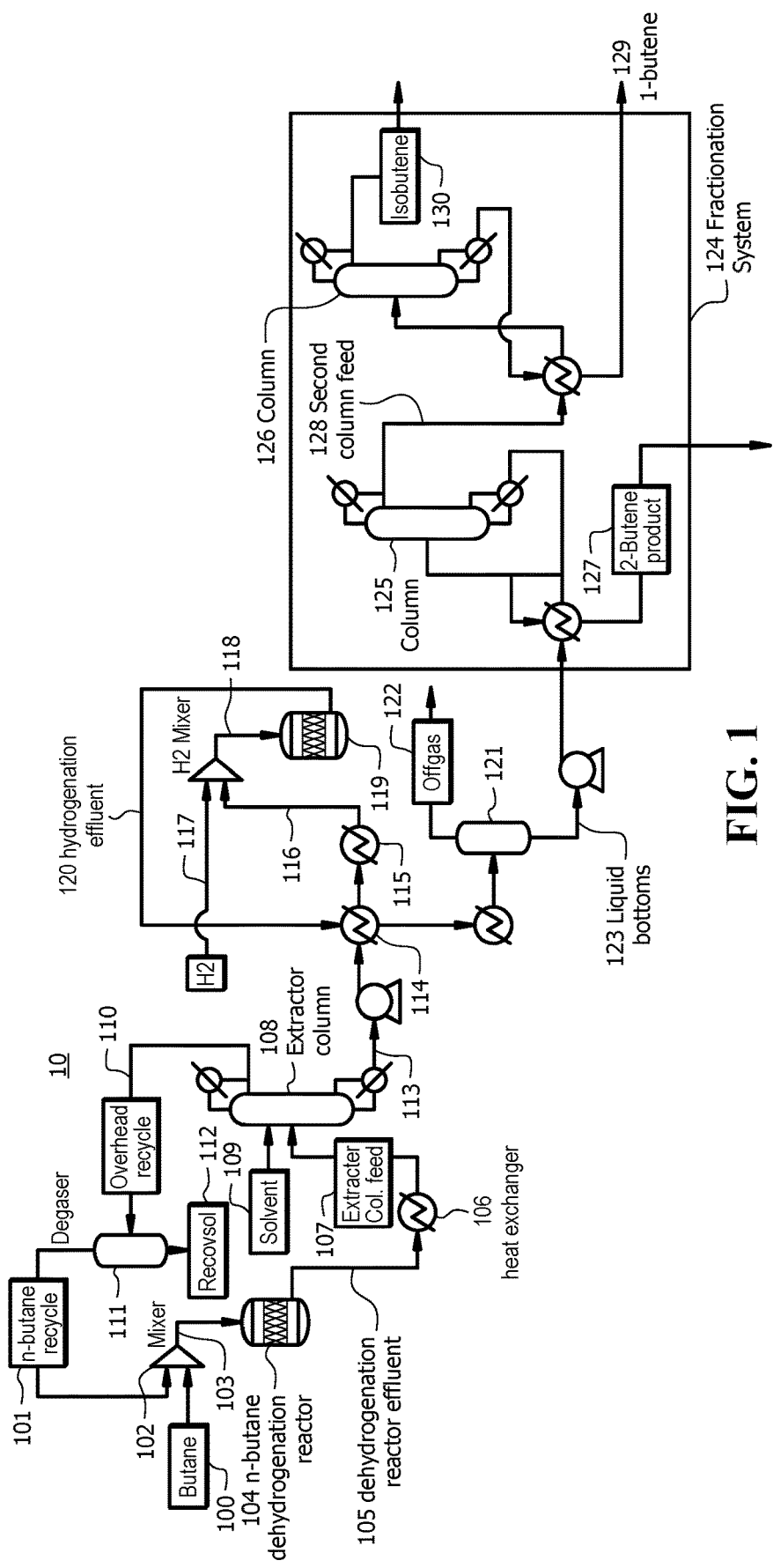
FIG. 1 is a system for producing butenes, according to embodiments of the invention.
Figure 2:
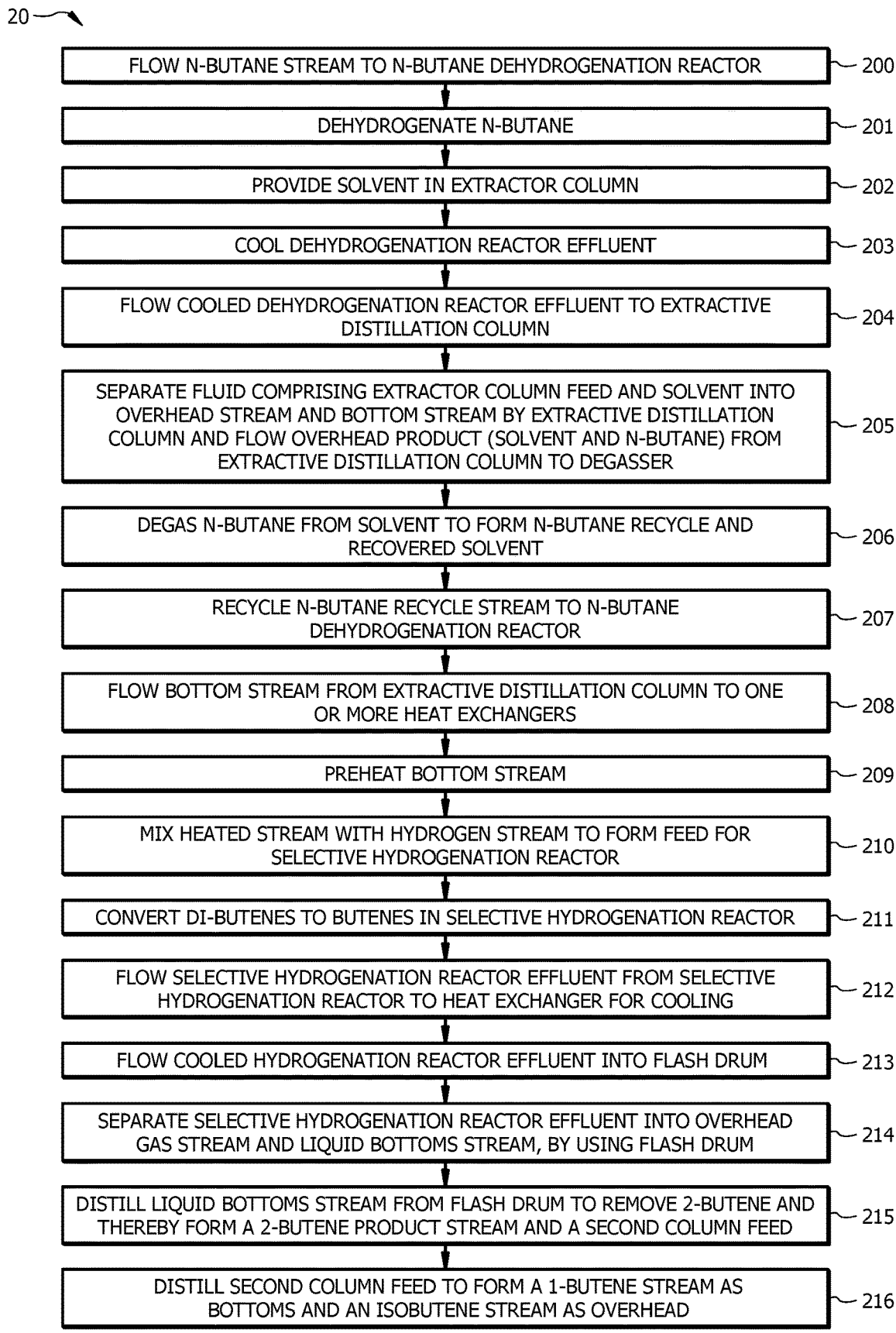
FIG. 2 is a method for producing butenes, according to embodiments of the invention.

FIG. 1 shows system 10 for producing butenes, according to embodiments of the invention. FIG. 2 shows method 20 for producing butenes, according to embodiments of the invention. Method 20 may be implemented using system 10.

Method 20, as implemented by system 10, can include flowing n-butane stream 100 to n-butane dehydrogenation reactor 104, at block 200. N-butane stream 100, in embodiments of the invention, can be flowed to n-butane dehydrogenation reactor 104 along with n-butane recycle stream 101, having been mixed by mixer 102 to produce mixed n-butane stream 103.

According to embodiments of the invention, mixed n-butane stream 103 comprises 100 wt. % to 10 wt. % of n-butane stream 100 and 0 wt. % to 70 wt. % of n-butane recycle stream 101. N-butane stream 100, in embodiments of the invention, comprises 5 to 100 wt. % n-butane, while n-butane recycle stream 101 comprises 60 to 70 wt. % n-butane in embodiments of the invention.

N-butane dehydrogenation reactor 104 is adapted to dehydrogenate n-butane to form butenes. According to embodiments of the invention, n-butane dehydrogenation reactor 104 includes a catalyst bed having a catalyst selective for the dehydrogenation reaction of n-butane to form butenes.

Method 20, in embodiments of the invention, includes block 201, which involves dehydrogenating n-butane of mixed n-butane stream 103 to form butenes. Typically, n-butane dehydrogenation processes leave some n-butane unconverted. So according to embodiments of the invention, the n-butane fed to n-butane dehydrogenation reactor 104 that is not dehydrogenated is flowed from n-butane dehydrogenation reactor 104 as a component of dehydrogenation reactor effluent 105. According to embodiments of the invention, dehydrogenation reactor effluent 105 comprises 60 to 70 wt. % n-butane, 25 to 35 wt. % 1-butene, and 65 v to 75 wt. % 2-butene.

Method 20 further involves, at block 202, providing solvent 109 (e.g., soya bean oil) in extractor column 108, according to embodiments of the invention. Solvent 109 can be provided by flowing it to solvent compartment by fed pump of extractor column 108.

According to embodiments of the invention, butene products mixed with unconverted normal butane are cooled before entering the extractive distillation column containing solvent. For example, at block 203, method 20 involves cooling dehydrogenation reactor effluent 105 with heat exchanger 106 to form extractor column feed 107. In embodiments of the invention, dehydrogenation reactor effluent 105 is cooled such that extractor column feed 107 is t a temperature in a range of 20 to 60° C.

At block 204, in embodiments of the invention, method 20 involves flowing extractor column feed 107 (cooled dehydrogenation reactor effluent 105) to extractor column 108 (an extractive distillation column). In doing so, solvent 109 contacts extractor column feed 107 such that n-butane from extractor column feed 107 dissolves in solvent 109 (e.g., soya bean oil). Although reactor effluents from high n-butane conversion dehydrogenation reactors may not be a big risk for downstream processes due to less separation issues, the catalysts that have high butene selectivities run at low conversions, posing a protuberant separation problem downstream of the reactor. According to embodiments of the invention, for dehydrogenation reactions with low conversion, e.g., 30-40% conversion of n-butane to butene, an extractive solvent used in the process can solve the reactor downstream problems. Regarding method 20, solvent 109 can affect n-butane and butene components differently and, in this way, cause the difference in the boiling points of the components in the fluid mixture of solvent 109 and extractor column feed 107 to increase. For example, soya bean oil, used as solvent 109, has the ability to extract a large amount of unconverted n-butane from extractor column feed 107.

According to embodiments of the invention, extractor column 108, operated with soya bean oil as solvent 109 and operated at low a temperature range of 10 to 50° C., has the ability to dissolve about 70 wt. % of the n-butane from extractor column feed 107. In embodiments of the invention, extractor column 108 separates a fluid comprising extractor column feed 107 and solvent 109 into overhead stream 110 and bottom stream 113 by extractive distillation column 108 and overhead stream 110 (comprising solvent (e.g., soya bean oil) and n-butane as solute) is flowed from extractor column 108 to degasser 111, as shown at block 205. At block 206, in embodiments of the invention, degasser 111 degases n-butane from solvent 109 to form n-butane recycle stream 101 and recovered solvent 112. N-butane recycle stream 101 may be recycled to n-butane dehydrogenation reactor 104, at block 207. For example, n-butane recycle stream 101 may be routed to n-butane dehydrogenation reactor 104 directly or mixed with n-butane stream 100 by mixer 102, as shown in FIG. 1. Recovered solvent 112, according to embodiments of the invention, can be recycled to extractor column 108 for further use.

According to embodiments of the invention, separation of n-butane from extractor column feed 107, at block 205, forms bottom stream 113, which can be flowed from extractor column 108 to heat exchanger 114, as shown at block 208. Bottom stream 113, according to embodiments of the invention comprises di-butenes and butenes with minor traces of isobutene (which is very rare). In embodiments of the invention, bottom stream 113, comprises 25 to 35 wt. % 1-butene, 65 to 75 wt. % 2-butene and 2 to 5 wt. % isobutene.

In embodiments of the invention, at block 209, bottom stream 113 is preheated by heat exchangers 114 and 115 to form heated stream 116. According to embodiments of the invention, bottom stream 113 is heated to form heated stream 116 at a temperature in a range of 50 to 100° C. Heated stream 116 can then be mixed with hydrogen stream 117 to form selective hydrogenation reactor feed 118, at block 210. At block 211, in embodiments of the invention, selective hydrogenation reactor feed 118 is routed to selective hydrogenation reactor 119, which converts di-butenes to butenes (even though di-butenes are expected to be very small amounts). Selective hydrogenation reactor effluent 120 is flowed from selective hydrogenation reactor 119 and cooled (e.g., by using it as heating medium in heat exchanger 114), at block 212, in embodiments of the invention. At block 213, after being cooled, selective hydrogenation reactor effluent 120 is flowed into flash drum 121, according to embodiments of the invention.

At block 214, flash drum 121 separates selective hydrogenation reactor effluent 120 into overhead gas stream 122 and liquid bottoms stream 123. Overhead gas stream 122 from flash drum 121 may be used as fuel while liquid bottoms stream 123 comprises the primary products, namely, a mixture of isobutene and 1-butene and 2-butene. In embodiments of the invention, liquid bottoms stream 123 comprises 25 to 35 wt. % 1-butene, 65 to 75 wt. % 2-butene and 2 to 5 wt. % isobutene. Liquid bottoms stream 123 may then be processed in fractionation system 124, in embodiments of the invention. Fractionation system 124 may be a two tower fractionation system. In embodiments of the invention, fractionation system 124 comprises large columns, column 125 and column 126, about the size of 200 trays each built with two shells.

In embodiments of the invention, column 125 removes, by distillation, 2-butene from liquid bottoms stream 123 to thereby form 2-butene product stream 127 and second column feed 128, as shown at block 215. Operating conditions for column 125, in embodiments of the invention include temperature in the range of 50-70° C. and pressure in the range of 2.5 to 7.5 bar. According to embodiments of the invention 2-butene product stream 127 comprises 0 to 1 wt. % 1-butene, and 80 to 90 wt. % 2-butene. According to embodiments of the invention, second column feed 128 comprises 90 to 99 wt. % 1-butene, and 0 to 1 wt. % isobutene. At block 216, column 126, by distillation, separates second column feed 128 into 1-butene stream 129 as bottoms and isobutene stream 130 as overhead. Operating conditions for column 126, in embodiments of the invention include temperature in the range of 35-45° C. and pressure in the range of 7 to 10 bar. According to embodiments of the invention, 1-butene stream 129 comprises 90 to 99 wt. % 1-butene. According to embodiments of the invention, isobutene stream 130 comprises 90 to 100 wt. % isobutene.

Method 20 as described above is an efficient downstream separation of unconverted normal butane feed and butene products that solves the problem of inseparability of feed from products in the production of butenes by n-butane dehydrogenation. This can be helpful for large scale production of butenes from cheap normal butane feedstock which was not achievable before in an economically viable manner.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

In the context of the present invention, embodiments 1-16 are described. Embodiment 1 is a method of producing butane. The method includes dehydrogenating, in a dehydrogenation reactor, a feed stream containing primarily n-butane to produce an intermediate product stream containing n-butane and one or more butenes. The method also includes contacting the intermediate product stream with a solvent that is more selective for dissolving the n-butane than for dissolving the one or more butenes to form a fluid that includes (1) a first portion including primarily the solvent and the n-butane, collectively, and (2) a second portion including primarily the one or more butenes. The method further includes separating the fluid to produce a recycle stream containing primarily the solvent and the n-butane, collectively, and a product stream containing primarily the one or more butenes. Embodiment 2 is the method of embodiment 1, wherein the solvent includes soya bean oil. Embodiment 3 is the method of either of embodiments 1 or 2, further including flowing the intermediate product stream to an extractive distillation column in which the solvent is disposed. Embodiment 4 is the method of embodiment 3, wherein the separating includes distilling the fluid in the extractive distillation column under conditions sufficient to produce an extractor overhead stream containing primarily the solvent and the n-butane, collectively, and an extractor bottom stream containing primarily the one or more butenes. Embodiment 5 is the method of embodiment 4, further including separating the extractor overhead stream into a n-butane recycle stream containing primarily n-butane and a recovered solvent stream containing primarily solvent. Embodiment 6 is the method of embodiment 5, wherein the recovered solvent stream is recycled to the extractive distillation column. Embodiment 7 is the method of embodiment 6 further including feeding the n-butane recycle stream to the dehydrogenation reactor. Embodiment 8 is the method of embodiment 7, further including processing the extractor bottom stream to form a product containing at least 92 wt. % 2-butene. Embodiment 9 is the method of embodiment 7, further including processing the extractor bottom stream to form a product containing at least to 99.7 wt. % 1-butene. Embodiment 10 is the method of any of embodiments 3 to 9, wherein conditions in the extractive distillation column include a temperature in a range of 10 to 60° C. Embodiment 11 is the method of any of embodiments 3 to 10, wherein conditions in the extractive distillation column include a pressure in a range of 0.01 to 1 MPa. Embodiment 12 is the method of any of embodiments 1 to 11, wherein the solvent dissolves 10 to 100 wt. % of the n-butane of the intermediate product stream and only 0.001 to 0.002 wt. % of the one or more butenes of the intermediate product stream is dissolved in the solvent. Embodiment 13 is the method of any of embodiments 1 to 12, wherein the feed stream contains 50 to 60 wt. % n-butane and 40 to 50 wt. % butenes. Embodiment 14 is the method of any of claims 1 to 13, wherein the one or more butenes contain 1-butene, 2-butene, trans butene, or combinations thereof.

Embodiment 15 is a method of producing butane. The method includes dehydrogenating, in a dehydrogenation reactor, a feed stream containing primarily n-butane to produce an intermediate product stream containing n-butane and one or more butenes. The method also includes flowing the intermediate product stream to an extractive distillation column in which soya bean oil is disposed. The method further includes contacting the intermediate product stream with the soya bean oil, the soya bean oil being more selective for dissolving the n-butane than for dissolving the one or more butenes, the contacting forming a fluid that includes (1) a first portion containing primarily the soya bean oil and the n-butane, collectively, and (2) a second portion containing primarily the one or more butenes. In addition, the method includes distilling the fluid in the extractive distillation column under conditions sufficient to produce an extractor overhead stream containing primarily the soya bean oil and the n-butane, collectively, and an extractor bottom stream containing primarily the one or more butenes.

Embodiment 16 is a method of producing butane. The method includes dehydrogenating, in a dehydrogenation reactor, a feed stream containing primarily n-butane to produce an intermediate product stream containing n-butane and one or more butenes. The method also includes flowing the intermediate product stream to an extractive distillation column in which soya bean oil is disposed. The method further includes contacting the intermediate product stream with the soya bean oil, the soya bean oil being more selective for dissolving the n-butane than for dissolving the one or more butenes, the contacting forming a fluid that includes (1) a first portion containing primarily the soya bean oil and the n-butane, collectively, and (2) a second portion containing primarily the one or more butenes. In addition, the method includes distilling the fluid in the extractive distillation column under conditions sufficient to produce an extractor overhead stream containing primarily the soya bean oil and the n-butane, collectively, and an extractor bottom stream containing primarily the one or more butenes. The method further includes separating the extractor overhead stream into a n-butane recycle stream containing primarily n-butane and a recovered soybean oil stream containing primarily soybean oil, and feeding the n-butane recycle stream to the dehydrogenation reactor. Further, the method includes processing the extractor bottom stream to form a product containing 92 wt. % to 99.7 wt. % butene.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of producing butene, the method comprising:
dehydrogenating, in a dehydrogenation reactor, a feed stream comprising primarily n-butane to produce an intermediate product stream comprising n-butane and one or more butenes;
contacting the intermediate product stream with a solvent that is more selective for dissolving the n-butane than for dissolving the one or more butenes to form a fluid that comprises (1) a first portion comprising primarily the solvent and the n-butane, collectively, and (2) a second portion comprising primarily the one or more butenes;
separating the fluid to produce a stream comprising primarily the solvent and the n-butane, collectively, and a product stream comprising primarily the one or more butenes;
wherein the solvent comprises soya bean oil.

2. The method of claim 1, further comprising:
flowing the intermediate product stream to an extractive distillation column in which the solvent is disposed.

3. The method of claim 2, wherein the separating comprises:
distilling the fluid in the extractive distillation column under conditions sufficient to produce an extractor overhead stream comprising primarily the solvent and the n-butane, collectively, and an extractor bottom stream comprising primarily the one or more butenes.

4. The method of claim 3, further comprising:
separating the extractor overhead stream into a n-butane recycle stream comprising primarily n-butane and a recovered solvent stream comprising primarily solvent.

5. The method of claim 4, wherein the recovered solvent stream is recycled to the extractive distillation column.

6. The method of claim 5 further comprising:
feeding the n-butane recycle stream to the dehydrogenation reactor.

7. The method of claim 6, further comprising:
processing the extractor bottom stream to form a product comprising at least 92 wt. % 2-butene.

8. The method of claim 6, further comprising:
processing the extractor bottom stream to form a product comprising at least to 99.7 wt. % 1-butene.

9. The method of claim 3, wherein the one or more butenes comprise 1-butene, 2-butene, trans butene, or combinations thereof.

10. The method of claim 4, wherein the one or more butenes comprise 1-butene, 2-butene, trans butene, or combinations thereof.

11. The method of claim 5, wherein the one or more butenes comprise 1-butene, 2-butene, trans butene, or combinations thereof.

12. The method of claim 2, wherein conditions in the extractive distillation column include a temperature in a range of 10 to 50° C.

13. The method of claim 2, wherein conditions in the extractive distillation column include a pressure in a range of 0.01 to 1 MPa.

14. The method of claim 2, wherein the one or more butenes comprise 1-butene, 2-butene, trans butene, or combinations thereof.

15. The method of claim 1, wherein the solvent dissolves 10 to 100 wt. % of the n-butane of the intermediate product stream and only 0.001 to 0.002 wt. % of the one or more butenes of the intermediate product stream is dissolved in the solvent.

16. The method of claim 1, wherein the feed stream comprises 50 to 60 wt. % n-butane and 40 to 50 wt. % butenes.

17. The method of claim 1, wherein the one or more butenes comprise 1-butene, 2-butene, trans butene, or combinations thereof.

18. A method of producing butene, the method comprising:

dehydrogenating, in a dehydrogenation reactor, a feed stream comprising primarily n-butane to produce an intermediate product stream comprising n-butane and one or more butenes;

flowing the intermediate product stream to an extractive distillation column in which soya bean oil is disposed;

contacting the intermediate product stream with the soya bean oil, the soya bean oil being more selective for dissolving the n-butane than for dissolving the one or more butenes, the contacting forming a fluid that comprises (1) a first portion comprising primarily the soya bean oil and the n-butane, collectively, and (2) a second portion comprising primarily the one or more butenes; and distilling the fluid in the extractive distillation column under conditions sufficient to produce an extractor overhead stream comprising primarily the soya bean oil and the n-butane, collectively, and an extractor bottom stream comprising primarily the one or more butenes.

19. A method of producing butene, the method comprising:

dehydrogenating, in a dehydrogenation reactor, a feed stream comprising primarily n-butane to produce an intermediate product stream comprising n-butane and one or more butenes;

flowing the intermediate product stream to an extractive distillation column in which soya bean oil is disposed;

contacting the intermediate product stream with the soya bean oil, the soya bean oil being more selective for dissolving the n-butane than for dissolving the one or more butenes, the contacting forming a fluid that comprises (1) a first portion comprising primarily the soya bean oil and the n-butane, collectively, and (2) a second portion comprising primarily the one or more butenes;

distilling the fluid in the extractive distillation column under conditions sufficient to produce an extractor overhead stream comprising primarily the soya bean oil and the n-butane, collectively, and an extractor bottom stream comprising primarily the one or more butenes;

separating the extractor overhead stream into a n-butane recycle stream comprising primarily n-butane and a recovered soybean oil stream comprising primarily soybean oil;

feeding the n-butane recycle stream to the dehydrogenation reactor; and processing the extractor bottom stream to form a product comprising 92 wt. % to 99.7 wt. % butene.

\* \* \* \* \*